US009663412B2

(12) United States Patent
Thompson

(10) Patent No.: US 9,663,412 B2
(45) Date of Patent: May 30, 2017

(54) UREA FERTILIZER COMPOSITIONS COMPRISING RICE HULLS AND METHODS OF USE

(71) Applicant: OMS Investments, Inc., Los Angeles, CA (US)

(72) Inventor: Harold Thompson, Powell, OH (US)

(73) Assignee: OMS Investments, Inc., Los Angeles, CA (US)

( * ) Notice: Subject to any disclaimer, the term of this patent is extended or adjusted under 35 U.S.C. 154(b) by 0 days.

(21) Appl. No.: 15/073,181

(22) Filed: Mar. 17, 2016

(65) Prior Publication Data

US 2016/0200638 A1    Jul. 14, 2016

Related U.S. Application Data

(63) Continuation of application No. 14/962,720, filed on Dec. 8, 2015, now abandoned.

(60) Provisional application No. 62/089,443, filed on Dec. 9, 2014.

(51) Int. Cl.
| | | |
|---|---|---|
| *C05G 3/00* | (2006.01) | |
| *A01N 39/02* | (2006.01) | |
| *A01N 39/04* | (2006.01) | |
| *C05C 9/02* | (2006.01) | |
| *C05G 3/02* | (2006.01) | |
| *A61L 9/013* | (2006.01) | |

(52) U.S. Cl.
CPC ........... *C05G 3/0088* (2013.01); *A01N 39/02* (2013.01); *A01N 39/04* (2013.01); *A61L 9/013* (2013.01); *C05C 9/02* (2013.01); *C05G 3/02* (2013.01)

(58) Field of Classification Search
CPC .. C05C 9/02; C05C 9/00; A01N 25/12; C05G 3/0058
See application file for complete search history.

(56) References Cited

U.S. PATENT DOCUMENTS

| | | | |
|---|---|---|---|
| 3,041,159 A | 6/1962 | Smith | |
| 3,076,700 A | 2/1963 | Renner | |
| 3,223,518 A | 12/1965 | Hansen | |
| 3,231,363 A | 1/1966 | Renner | |
| 3,325,276 A | 6/1967 | Feller | |
| 3,558,299 A | 1/1971 | Baskin | |
| 3,852,055 A | 12/1974 | Hawkes et al. | |
| 4,025,329 A | 5/1977 | Goertz | |
| 5,019,564 A * | 5/1991 | Lowe | A01K 1/0155 424/413 |

(Continued)

FOREIGN PATENT DOCUMENTS

| | | | |
|---|---|---|---|
| CN | 101366356 A | 2/2009 | |
| CN | 101486618 * | 7/2009 | ............... C05G 3/08 |

(Continued)

OTHER PUBLICATIONS

CN 101486618 human translation, Jun. 2016, p. 0-20.*
International Search Report for International Patent Application PCT/US15/64589 mailed Feb. 16, 2016.

*Primary Examiner* — Kortney L Klinkel
(74) *Attorney, Agent, or Firm* — Ulmer & Berne LLP

(57) ABSTRACT

Compositions comprising urea containing fertilizer (e.g., urea fertilizers or urea formaldehyde reaction product fertilizers such as urea-formaldehyde fertilizer or methylene urea fertilizers) and rice hulls, as well as methods of making and using such compositions are provided.

22 Claims, 9 Drawing Sheets

(56) References Cited

U.S. PATENT DOCUMENTS

| | | |
|---|---|---|
| 5,102,440 A | 4/1992 | Gallant et al. |
| 6,039,781 A | 3/2000 | Goertz et al. |
| 7,108,732 B2 | 9/2006 | Sakamoto et al. |
| 7,776,125 B2 | 8/2010 | Thompson |
| 8,492,444 B2 | 7/2013 | Hammond et al. |
| 2009/0093368 A1* | 4/2009 | Thompson ............. A01N 25/12 504/323 |

FOREIGN PATENT DOCUMENTS

| | | | |
|---|---|---|---|
| WO | 2012/129847 | 10/2012 | |
| WO | WO 2014/144724 | * 9/2014 | ............. A01N 39/04 |

* cited by examiner

UREA FERTILIZER COMPOSITIONS COMPRISING RICE HULLS AND METHODS OF USE

CROSS-REFERENCE TO RELATED APPLICATIONS

This application is a continuation of U.S. patent application Ser. No. 14/962,720, filed Dec. 8, 2015, which claims the benefit of U.S. Provisional Patent Application No. 62/089,443, filed Dec. 9, 2014, the disclosures of which are incorporated by reference herein in their entireties.

FIELD OF THE INVENTION

Compositions comprising urea fertilizer and rice hulls, as well as methods of making and using such compositions are provided.

BACKGROUND OF THE INVENTION

Urea containing fertilizer compositions (e.g., urea fertilizers or urea formaldehyde reaction product fertilizers such as urea-formaldehyde fertilizer or methylene urea fertilizers) have been known and used for many years. Urea containing fertilizers (e.g., urea fertilizers or urea formaldehyde reaction product fertilizers such as urea-formaldehyde fertilizer or methylene urea fertilizers) provide a high level of nitrogen availability, which is necessary to maintain growth and color of lawn turf. Examples of urea containing fertilizers (e.g., urea fertilizers or urea formaldehyde reaction product fertilizers such as urea-formaldehyde fertilizer or methylene urea fertilizers) are disclosed in U.S. Pat. Nos. 3,076,700; 3,231,363; 3,223,518; 4,025,329; 5,102,440; and 6,039,781, each of which are hereby incorporated by reference in their entireties.

Urea containing fertilizers (e.g., urea fertilizers or urea formaldehyde reaction product fertilizers such as urea-formaldehyde fertilizer or methylene urea fertilizers) in general, including solid or granulated urea containing fertilizers, have a tendency to cake or clump over time, such as during storage, causing problems in spreading and/or disseminating the resulting caked or clumped fertilizer products. See U.S. Pat. No. 7,776,125, hereby incorporated by reference in its entirety. Urea containing fertilizers, because they are hygroscopic, develop crystal bridges as they age under typical storage conditions. These crystal bridges result in hard caking and lump formation, thus making the fertilizer more difficult to use effectively. Urea crystal growth is a major component of urea containing fertilizers and one of the important driving forces in the caking process. Urea crystal growth also can develop so extensively that the entire particle surface is covered with urea crystals. When this occurs on fertilizer products containing surface applied active ingredients, overall active ingredient performance can be negatively affected. The net result is lower active ingredient control of weeds or other targeted pests.

Anti-caking agents and crystal modifiers are typically applied directly to the surface urea-containing fertilizers. For example, known anti-caking agents normally have been applied to the surface of the fertilizer particles, and due to inefficient coating techniques, have resulted in only partially coated granules, providing less than effective reduction in caking of the granules. In addition, over time, such surface applied coatings may break away from the granules, and thus the treatment slowly loses effectiveness. WO 2012/129847; U.S. Pat. Nos. 3,041,159; 3,325,276; 3,558,299; 3,852,055; 7,108,732; and 8,492,444, each of which are hereby incorporated by reference in their entireties. These materials have somewhat limited performance because of inefficient coating techniques, resulting in partially coated granules. In addition, over time the surface applied coating may break away from or strike into the granule and thus slowly lose effectiveness.

Solid anti-caking agents found in the art, such as vermiculite, are effective if larger quantities are utilized and the vermiculite is used as a parting agent. But if the vermiculite is granulated and covered with urea containing fertilizer resin, the anti-caking benefits are eliminated.

In sum, anti-caking agents and crystal modifiers known in the art have not satisfactorily solved the caking/clumping problems in urea containing fertilizers (e.g., urea fertilizers or urea formaldehyde reaction product fertilizers such as urea-formaldehyde fertilizer or methylene urea fertilizers).

SUMMARY OF VARIOUS EMBODIMENTS OF THE INVENTION

In one aspect, the invention relates to compositions comprising rice hulls and a urea containing fertilizer. These compositions show, among other things, less crystal formation and less clumping when stored over time, and reduced loss of usable product (e.g., herbicide), as compared to a urea containing fertilizer not comprising rice hulls.

In one embodiment, a fertilizer composition may comprise granules comprising rice hulls and a urea containing fertilizer. In an embodiment, the rice hulls may be comminuted in size. In an embodiment, the rice hulls may be ground. In an embodiment, the rice hulls may be about 20-70 SGN. In an embodiment, the rice hulls may be about 20-70 SGN, 30-60 SGN, 45-55 SGN, 30-50 SGN, 40-60 SGN, 45-50 SGN, or 50-55 SGN in size. In an embodiment, the rice hulls may be about 40-60 SGN. In an embodiment, the rice hulls may be about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 SGN in size. In an embodiment, the rice hulls may be about 50 SGN.

In one embodiment, when the fertilizer composition described herein is stored over a period of time between 1 and 8 months, for example 1, 2, 3, 4, 5, 6, 7, or 8 months, it may have a reduced crystal aspect ratio compared to a fertilizer composition not having rice hulls stored for the same period of time. In another embodiment, the crystal aspect ratio of the fertilizer composition described herein may be reduced to a level in a range from about 30:1 to about 4:1, for example, 30:1, 27:1, 25:1, 23:1, 20:1, 19:1, 17:1, 16:1, 15:1, 13:1, 10:1, 9:1, 8:1, 7:1, 6:1, 5:1, or 4:1. In another embodiment, the months of storage may be from between 2 and 8 months, for example 2, 3, 4, 5, 6, 7, or 8 months.

In one embodiment, the rice hulls may be about 1-50% by weight of the granule. In an embodiment, the rice hulls may be about 5-50%, 10-40%, 20-30%, 15-30%, 20-35%, 15-40%, 15-30%, 10-20%, 10-25%, 15-25%, 15-35%, 25-50%, or 15-50% by weight of the granule. In an embodiment, the rice hulls may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% by weight of the granule. In an embodiment, the rice hulls may be about 10-25% by weight of the granule. In an embodiment, the rice hulls may be about 20% by weight of the granules.

In any of the embodiments, the urea-based fertilizer may be a urea containing fertilizer resin (e.g., a resin of urea fertilizer or urea formaldehyde reaction product fertilizer such as urea-formaldehyde fertilizer or methylene urea fertilizers). In an embodiment, the urea containing fertilizer resin (e.g., a resin of urea fertilizer or urea formaldehyde reaction product fertilizer such as urea-formaldehyde fertilizer or methylene urea fertilizers) may have a urea to formaldehyde ratio of about 1.5:1 to about 8:1. In an embodiment, the ratio may be about 1.5:1, 2:1, 3:1, 4:1, 5:1, 6:1, 7:1, or 8:1. In an embodiment, the ratio may be about 4:1.

In one embodiment, the average crystal area of urea crystals formed in the fertilizer composition described herein after between 2 and 8 months, for example 2, 3, 4, 5, 6, 7, or 8 months, is less than 60 $\mu m^2$. In an embodiment, the average crystal area of urea crystals formed in the fertilizer composition described herein after between 2 and 8 months, for example 2, 3, 4, 5, 6, 7, or 8 months, may be less than 30, less than 35, less than 40, less than 45, less than 50, less than 55, or less than 60 $\mu m^2$.

In one embodiment, the fertilizer composition described herein may comprise less than 1, less than 2, less than 3, less than 4, less than 5, less than 6, less than 7, less than 8, less than 9, less than 10, less than 11, less than 12, less than 13, less than 14, less than 15, less than 16, less than 17, less than 18, less than 19, or less than 20% water by weight of the granule. In an embodiment, the composition may comprise less than 5% water by weight of the granule.

In other embodiments, the granules described herein may be about 1-5 mm in size. In other embodiment, the granules may be from about 0.5 to about 5 mm in size, for example 0.5, 0.75, 1, 2, 3, 4, or 5 mm in size. In other embodiment, the granules may be about 1-3, 1-5, 2-3, 0.75-3, 0.5-1, or 1-2 mm in size.

In the above embodiments, the composition may comprise granules comprising ground rice hulls coated with a urea containing fertilizer resin (e.g., a resin of urea fertilizer or urea formaldehyde reaction product fertilizer such as urea-formaldehyde fertilizer or methylene urea fertilizers), potassium sulfate, ammonium sulfate, 3,6-Dichloro-2-methoxybenzoic acid (dicamba), 2,4-dichlorophenoxy acetic acid (2,4-D), and methyl chlorophenoxy propionic acid (MCPP-P). In other embodiments, the granule may comprise 40-60% by weight urea containing fertilizer (e.g., urea fertilizers or urea formaldehyde reaction product fertilizers such as urea-formaldehyde fertilizer or methylene urea fertilizers). In other embodiments, the granule may comprise about 58% by weight urea containing fertilizer (e.g., urea fertilizers or urea formaldehyde reaction product fertilizers such as urea-formaldehyde fertilizer or methylene urea fertilizers). In other embodiments, the granule may comprise 10-25% by weight ground rice hulls. In other embodiments, the granule may comprise 20% by weight ground rice hulls. In other embodiments, the granule may comprise about 5-10% by weight potassium sulfate. In other embodiments, the granule may comprise about 6.5% by weight potassium sulfate. In other embodiments, the granule may comprise about 10-20% by weight ammonium sulfate. In other embodiments, the granule may comprise about 13.5% by weight ammonium sulfate. In other embodiments, the granule may comprise 0.5-4% by weight 2,4-dichlorophenoxy acetic acid (2,4-D). In other embodiments, the granule may comprise about 1.25% 2,4-dichlorophenoxy acetic acid (2,4-D). In other embodiments, the granule may comprise about 0.5-1.5% by weight methyl chlorophenoxy propionic acid (MCPP-P). In other embodiments, the granule may comprise about 0.7% methyl chlorophenoxy propionic acid (MCPP-P). In one embodiment, the granule may comprise about 0.04-0.2% by weight 3,6-Dichloro-2-methoxybenzoic acid (dicamba).

In the above embodiments, the fertilizer composition described herein may further comprise fertilizer components. In the above embodiments, the granules described herein may further comprise fertilizer components. In other embodiments, the fertilizer components may be potassium sulfate, micro elements, mono-ammonium phosphate, potassium chloride, or mixtures thereof. In other embodiments, the fertilizer component may be calcium nitrate, ammonium sulfate, coated urea (such as polymer coated urea or sulfur-coated urea), isobutylidene diurea, ammonium nitrate, urea-form, methylene urea, urea, anhydrous ammonia, ammonium polyphosphate, monoammonium phosphate, diammonium phosphate, potassium nitrate, or mixtures thereof.

In the above embodiments, the composition may further comprise herbicides, micronutrients, biostimulants, macronutrients, inert solid carriers, or mixtures thereof.

In the above embodiments, the granule further may comprise herbicides, micronutrients, biostimulants, macronutrients, inert solid carriers, or mixtures thereof.

In the above embodiments, the composition described herein may be a controlled release fertilizer.

In the above embodiments, the granule described herein may be a controlled release fertilizer.

In the above embodiments, the composition may comprise less than 1, less than 2, less than 3, less than 4, less than 5, less than 6, less than 7, less than 8, less than 9, less than 10, less than 11, less than 12, less than 13, less than 14, less than 15, less than 16, less than 17, less than 18, less than 19, or less than 20% water by weight of the composition. In other embodiments, the composition may comprise less than 5% water by weight of the composition.

In the above embodiments, the granule described herein may comprise less than 1, less than 2, less than 3, less than 4, less than 5, less than 6, less than 7, less than 8, less than 9, less than 10, less than 11, less than 12, less than 13, less than 14, less than 15, less than 16, less than 17, less than 18, less than 19, or less than 20% water by weight of the composition. In other embodiments, the granule may comprise less than 5% water by weight of the composition.

In the above embodiments, the composition described herein may produce less of an odor than a fertilizer with a similar amount of urea. In other embodiments, the composition may have an average odor concentration of less than 550 o.u./m$^3$.

In the above embodiments, the granules described herein may produce less of an odor than a fertilizer with a similar amount of urea. In other embodiments, the granules may have an average odor concentration of less than 550 o.u./m$^3$.

In the above embodiments, a soil amendment may comprise the fertilizer composition described herein.

In the above embodiments, a soil additive may comprise the fertilizer composition described herein.

In the above embodiments, a method of fertilizing a plant may comprise adding the fertilizer composition described herein to a plant.

In the above embodiments, a method of feeding a plant may comprise adding the fertilizer composition described herein to a plant.

In the above embodiments, a method of promoting plant growth may comprise administering the fertilizer composition described herein to a plant life. In other embodiments, the plant life may be a plant, plant cutting, or seed. In other embodiments, the plant may be young plant, transplant, or seedling.

In the above embodiments, a method of making a soil may comprise admixing the fertilizer composition described herein with a soil.

In the above embodiments, a soil may comprise the fertilizer composition described herein.

In the above embodiments, a method of amending a soil may comprise admixing the fertilizer composition described herein with a soil.

In the above embodiments, a method of making a fertilizer composition with fewer urea crystals as compared to a fertilizer not comprising rice hulls may comprise spraying urea containing fertilizer resin (e.g., a resin of urea fertilizers or urea formaldehyde reaction product fertilizers such as urea-formaldehyde fertilizer or methylene urea fertilizers) onto rice hulls and forming a granule. In other embodiments, the fertilizer composition has about 10-30% fewer urea crystals than a fertilizer not comprising rice hulls.

In the above embodiments, a method of making the fertilizer composition may comprise spraying molten urea containing fertilizer resin (e.g., a resin of urea fertilizers or urea formaldehyde reaction product fertilizers such as urea-formaldehyde fertilizer or methylene urea fertilizers) onto rice hulls and forming a granule. In other embodiments, the rice may be hulled by dry milling or parboiling. In other embodiments, the rice may be hulled by dry milling. In other embodiments, the method may further comprise comminuting the rice hulls in size. In other embodiments, the method may further comprise adding fertilizer nutrients. In other embodiments, the fertilizer nutrients may be potassium sulfate, micro elements, mono-ammonium phosphate, potassium chloride, or mixtures thereof. In other embodiments, the fertilizer is granular. In other embodiments, the granulation may be done in a rotating drum, fluidized bed, pan, pellet mill, or a combination thereof. In other embodiments, the granulation may be performed at a temperature from about 130-160° F. In other embodiments, the molten urea containing fertilizer resin (e.g., a resin of urea fertilizers or urea formaldehyde reaction product fertilizers such as urea-formaldehyde fertilizer or methylene urea fertilizers) may be at a temperature of about 270-275° F.

In the above embodiments, a method for reducing the crystal aspect ratio of crystals formed in a fertilizer may comprise adding rice hulls in an amount sufficient to lower the crystal aspect ratios of the crystals formed in the fertilizer after storage. In other embodiments, the crystal aspect ratios of the crystals formed in the urea containing fertilizer (e.g., urea fertilizers or urea formaldehyde reaction product fertilizers such as urea-formaldehyde fertilizer or methylene urea fertilizers) may be reduced to a level in a range from about 30:1 to about 4:1, for example, 30:1, 27:1, 25:1, 23:1, 20:1, 19:1, 17:1, 16:1, 15:1, 13:1, 10:1, 9:1, 8:1, 7:1, 6:1, 5:1, or 4:1. In another embodiment, the crystal aspect ratios of the crystals formed in the urea containing fertilizer (e.g., urea fertilizers or urea formaldehyde reaction product fertilizers such as urea-formaldehyde fertilizer or methylene urea fertilizers) may be reduced after from about 1 to about 8 months of storage, for example 1, 2, 3, 4, 5, 6, 7, or 8 months as compared a fertilizer not comprising rice hulls.

In the above embodiments, a method for reducing the number of urea crystals formed in a fertilizer may comprise adding rice hulls in an amount sufficient to lower the crystal aspect ratios of the crystals formed in the fertilizer after storage. In another embodiment, the number of urea crystals formed in the urea containing fertilizer (e.g., urea fertilizers or urea formaldehyde reaction product fertilizers such as urea-formaldehyde fertilizer or methylene urea fertilizers) may be reduced by about 10-40% as compared to a fertilizer not comprising rice hulls. In another embodiment, the number of urea crystals formed in the urea containing fertilizer (e.g., urea fertilizers or urea formaldehyde reaction product fertilizers such as urea-formaldehyde fertilizer or methylene urea fertilizers) may be reduced by about 30% as compared to a fertilizer not comprising rice hulls. In another embodiment, the number of urea crystals formed in the urea containing fertilizer (e.g., urea fertilizers or urea formaldehyde reaction product fertilizers such as urea-formaldehyde fertilizer or methylene urea fertilizers) may be reduced after about 1-8 months of storage as compared a fertilizer not comprising rice hulls.

BRIEF DESCRIPTION OF THE DRAWINGS

FIG. 1A is a urea formaldehyde reaction product granule surface that has been completely covered with urea crystals during the aging process. Even the areas where active ingredient was applied (brighter white areas) are covered with urea crystals.

FIG. 1B is a surface of a urea formaldehyde reaction product granule comprising ground rice hulls. This formulation has significantly fewer urea crystal growth over the same aging process period and, in particular, appears to contain no crystals growing over the active ingredient cover areas (brighter white areas).

FIG. 2A shows that the formulation containing vermiculite had almost five-times more lumps than the sample formulated with ground rice hulls when compared using the non-dropped lumps test. Statistical analysis demonstrated this difference was significant.

FIG. 2B shows the formulation containing vermiculite had approximately forty-four times as many lumps than the sample formulated with ground rice hulls when compared using the dropped lumps test. Statistical analysis demonstrated this difference was significant.

FIG. 4A shows the X-ray analysis of the silicon and shows that the silica is located in tight bans on the surface of the rice hulls.

FIG. 4B reflects the X-ray analysis of the carbon and, shows that, in contrast, the carbon is dispersed throughout the surface of the rice hull.

DETAILED DESCRIPTION OF PREFERRED EMBODIMENTS

Figure 1A:
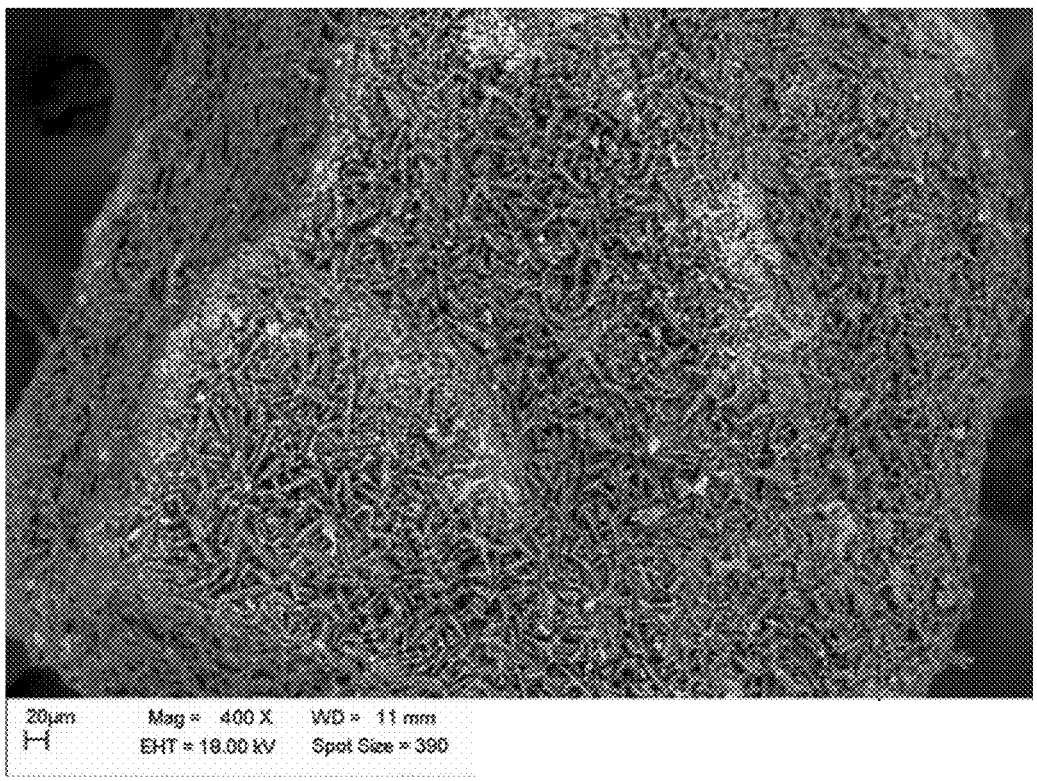
FIG. 1A depicts Scanning Electron Micrographs (SEM) images of the surface of granulated urea formaldehyde reaction product particle that have been aged for over five months.
Figure 1B:
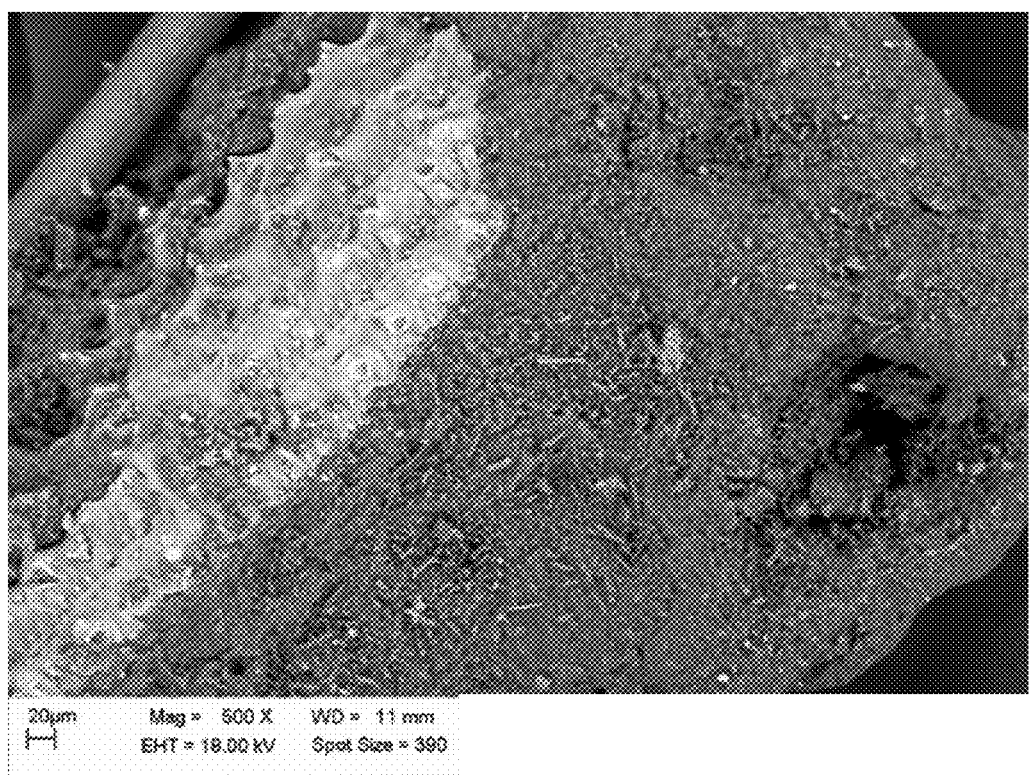
FIG. 1B depicts Scanning Electron Micrographs (SEM) images of the surface of granulated urea formaldehyde reaction product particle that have been aged for over five months.

The invention provides for compositions comprising rice hulls and a urea-based fertilizer, methods of making the compositions, and methods of using the compositions.

Definitions

Unless defined otherwise, all technical and scientific terms used herein have the same meaning as those commonly understood by one of ordinary skill in the art to which this invention belongs.

As used in the description herein and throughout the claims that follow, the meaning of "a," "an," and "the" includes plural reference unless the context clearly dictates otherwise.

"Crystal aspect ratio," as used herein, refers broadly to the length to width ratio of a urea crystal, e.g., a urea crystal with a crystal aspect ratio of 50:1 is 50 times as long as it is wide.

"NPK rating," as used herein, refers broadly to a labeling scheme for describing the amount of nitrogen, phosphorus, and potassium. NPK ratings consist of three numbers separated by dashes (e.g., 10-10-10 or 16-4-8) describes the chemical content of fertilizers. The first number represents the percentage of nitrogen in the product; the second number represents the percentage of phosphorous in the product; the third number represents the percentage of potassium in the product. The common form is "N—P—K."

"SGN," as used herein, refers broadly to Size Guide Number (SGN). The SGN is determined by calculating the average particle size of a product granules in millimeters (mm) and multiplying by 100. For example, 100 SGN=1 mm and 1 SGN=10 ☐m.

Rice Hulls Reduce Caking and Crystal Formation in Urea Containing Fertilizer

The inventor surprisingly discovered, among other things, that the use of ground rice hulls reduces the caking potential of a granulated fertilizer (e.g., comprising urea containing fertilizer resin). Specifically, the inventor surprisingly found that adding ground rice hulls to a urea containing fertilizer (e.g., urea fertilizers or urea formaldehyde reaction product fertilizers such as urea-formaldehyde fertilizer or methylene urea fertilizers) reduced urea crystal growth over time, which, in turn, helps prevent the development of crystal bridges that form the base elements for product caking. The synergistic combination of ground rice hulls and urea containing fertilizer (e.g., urea fertilizers or urea formaldehyde reaction product fertilizers such as urea-formaldehyde fertilizer or methylene urea fertilizers) results in reduced urea crystal growth during storage of urea containing fertilizer. The lower urea crystal growth also protects any surface-applied active ingredients (e.g., herbicides), since crystals will no longer cover the particle surface. The rice hull based fertilizer granule makes a surprisingly good substrate for transporting active ingredient due to its relatively small particle size, low bulk density, and relatively high absorptivity. Further, the fertilizer compositions described herein also have a lower average odor concentration as measured by odor unit per cubic meter of air (1 o.u./m$^3$) than other fertilizer compositions that do not comprise rice hulls.

Crystal growth in urea-containing fertilizers is a major factor that causes caking of such fertilizers over time. For example, when grown from relatively pure solutions, urea crystallizes into long needles having length to width ratios (crystal aspect ratios) that can exceed 50:1. It is believed that these high crystal aspect ratios contribute significantly to the development of hard caking during typical storage of fertilizers, particularly urea containing fertilizer (e.g., urea fertilizers or urea formaldehyde reaction product fertilizers such as urea-formaldehyde fertilizer or methylene urea fertilizers).

Furthermore, when grown from solutions containing methylene urea and/or urea-formaldehyde polymer chains, urea will crystallize into long needles. See, e.g., Davey, et al. *Journal of Crystal Growth* 79 (1986): 607-613. These long crystal needles contribute to the development of hard caking during storage of urea containing fertilizers (e.g., urea fertilizers or urea formaldehyde reaction product fertilizers such as urea-formaldehyde fertilizer or methylene urea fertilizers). It is believed that outward growth of such long crystal needles from the surface of fertilizer particles enables them to bond with outwardly growing crystal needles of other particles causing caking or clumping effects. For example, the ability of urea crystals to achieve the crystal aspect ratios described above causes the urea particles to bond with other particles causing the particles to lock together into concrete-like lumps over time.

Without wishing to be bound to a specific theory, it is believed that the rice hulls change the properties of the urea containing fertilizer (e.g., urea fertilizers or urea formaldehyde reaction product fertilizers such as urea-formaldehyde fertilizer or methylene urea fertilizers). The rice hulls contain a significant amount of amorphous silica (e.g., about 20% by weight), which blocks crystal growth during storage of the fertilizer product. The rice hull amorphous silica interacts with the urea containing fertilizer (e.g., urea fertilizers or urea formaldehyde reaction product fertilizers such as urea-formaldehyde fertilizer or methylene urea fertilizers) and may disrupt the order required for crystallization, thus interfering with the crystal growth and not merely physically mixed with the urea containing fertilizer (e.g., urea fertilizers or urea formaldehyde reaction product fertilizers such as urea-formaldehyde fertilizer or methylene urea fertilizers).

The inventor has also surprisingly found that the fertilizer compositions described herein improve active ingredient effectiveness and product performance. The fertilizer compositions described herein synergistically provide the active ingredient more quickly and effectively. The fertilizer compositions described herein provide an unexpected advantage over the prior art technology because they reduce caking during product storage, and achieve greater active ingredient delivery, resulting in overall improved performance. Thus, the fertilizer compositions described herein result in the delivery of the active ingredient more quickly and effectively than prior art compositions. In field applications, the urea crystals must dissolve before active ingredient will come in contact with the leaf surface of target plant. Since only a limited amount of leaf surface moisture is available, in many prior art products, the active ingredient will never contact the leaf surface, leading to decreased active ingredient performance.

Rice Hulls

Rice hulls (or rice husks) are the hard protecting coverings of rice grains. The hull is formed from hard materials, including opaline silica and lignin, and protects the rice seed during the growing season. The rice hull contains about 40-50 percent cellulose, 25-30 percent lignin, and 15-20 percent opaline silica, which, together forms a polymeric material within rice hull. During the milling processes, the hulls are removed from the raw grain to yield whole brown rice, which may then be further milled to remove the bran layer, resulting in white rice.

To form a rice hull, the rice plant take up a soluble silica from the soil in the form of monosilicic acid and begins storing it in the hull. As the hulls ages, hydrogen bonding between the hydroxyl groups in the silicic acid and cellulose and lignin becomes established;

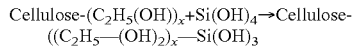

With further aging, water evaporation begins and the silicic acid polymerizes with the formation of siloxane bonds

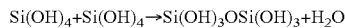

As polymerization and further water loss continues, amorphous silica begins to precipitate within the hull, and with continued moisture loss the opaline silica containing cellulose based polymer forms. Such a high concentration of silica is very unusual in nature, and the polymeric combination of silica and cellulose-lignin creates a material that is highly resistant to water penetration and fungal decay. The rice hulls also have a more acidic pH. The chemical composition and structure of the ground rice hulls is markedly different from the rice as it exists in nature.

Figure 3A:
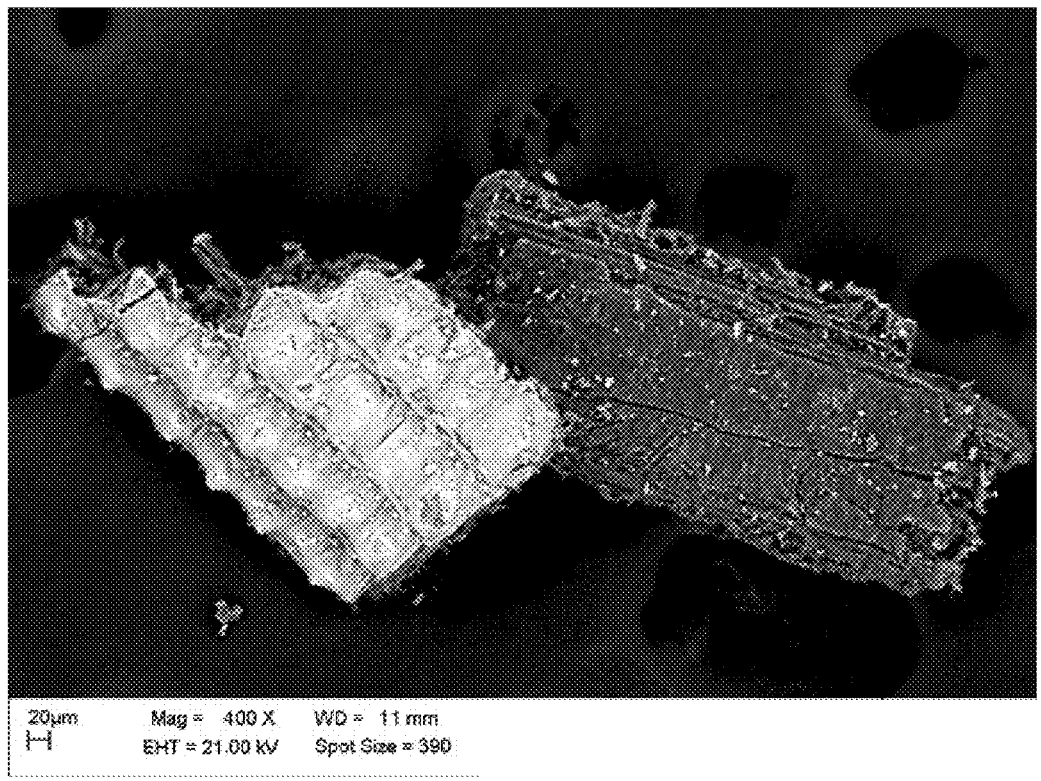
FIG. 3A depicts the surface of a rice hull.
Figure 3B:
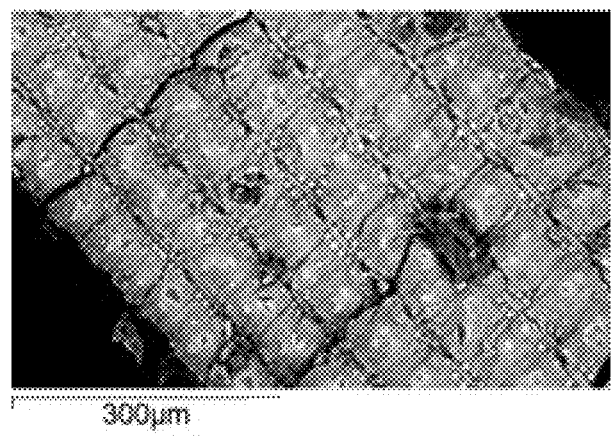
FIG. 3B depicts the cross-section of a rice hull.
Figure 3C:
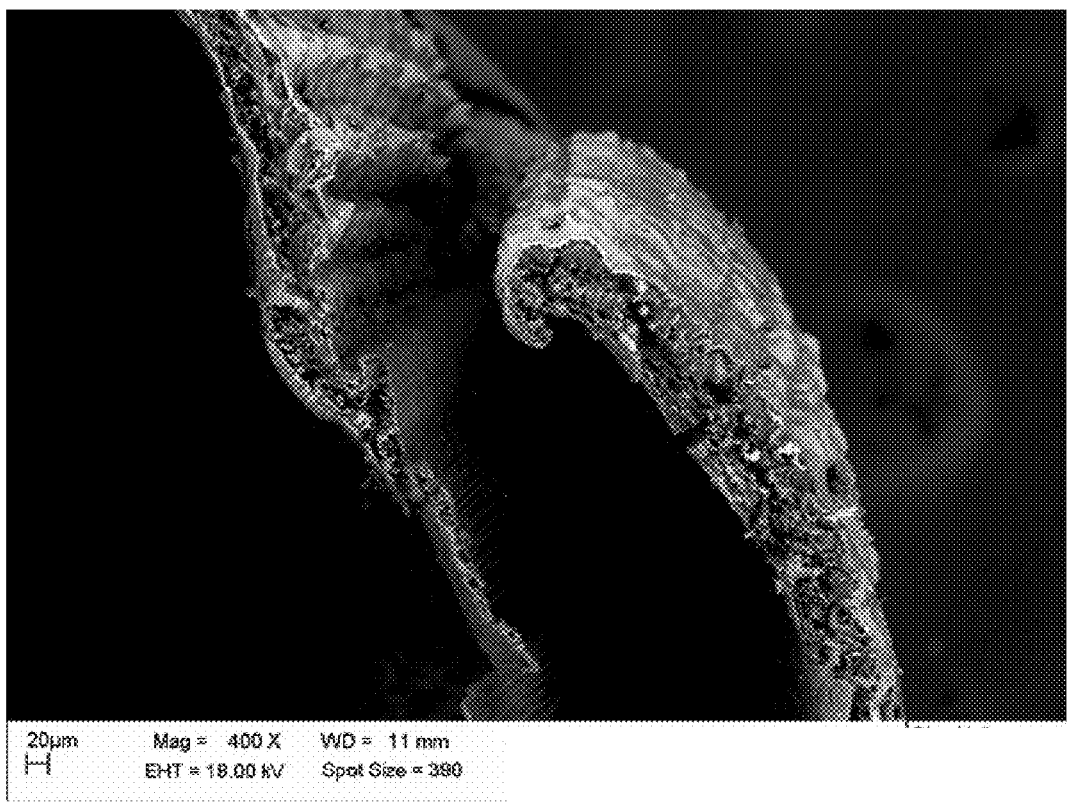
FIG. 3C depicts that the silica concentration is concentrated on the surface of the rice hull and is very thin.

In order to further define the compositional properties of rice hulls, a rice hull was examined using scanning electron microscopy with a backscatter detector. The backscatter detector allows for the differentiated between areas with higher and lower atomic number areas. The top portion of a rice hull showed a high concentration of silicon formed the opaline silica deposits (FIG. 3A). This silica deposit does exist throughout the entire rice hull (FIG. 3B). The inventor found that the hulls contain only a thin layer of polymeric silica-cellulose on the very outside (FIG. 3C).

Figure 4A:
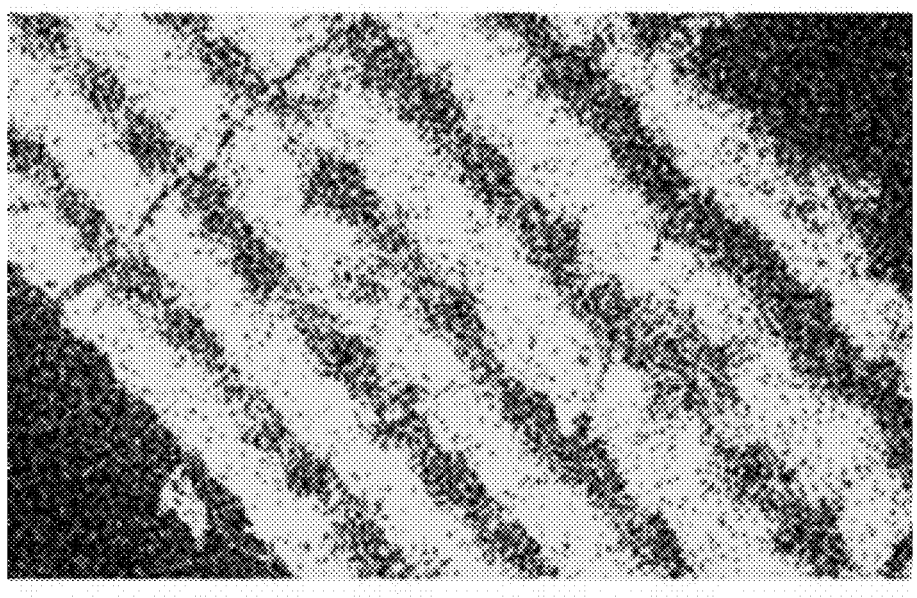
FIG. 4A depicts an elemental map for silicon and carbon of the rice hull surface.
Figure 4B:
FIG. 4B depicts an elemental map for silicon and carbon of the rice hull surface.

An x-ray detector was used to identify the elemental composition of a specific electron image. This analysis confirmed the presence of the opaline silica cellulose polymer as carbon appears uniformly dispersed within the area that also display bands of silicon (FIGS. 4A-B).

Without wishing to be bound to a specific theory, the inventor believes that the distribution of the silica in bands on the surface of the rice hulls provides for direct contact with the urea containing fertilizer (e.g., urea fertilizers or urea formaldehyde reaction product fertilizers such as urea-formaldehyde fertilizer or methylene urea fertilizers). This direct contact between areas of high silica concentration and the urea containing fertilizer (e.g., urea fertilizers or urea formaldehyde reaction product fertilizers such as urea-formaldehyde fertilizer or methylene urea fertilizers) inhibits the formation of urea crystals. This is in contrast with vermiculite, a hydrous silicate mineral, where the silica is more evenly distributed throughout the mineral structure. Both whole rice grains and vermiculite have been used as parting agents in urea containing fertilizer (e.g., urea fertilizers or urea formaldehyde reaction product fertilizers such as urea-formaldehyde fertilizer or methylene urea fertilizers). However, unlike rice hulls, when vermiculite is coated with urea containing fertilizer (e.g., urea fertilizers or urea formaldehyde reaction product fertilizers such as urea-formaldehyde fertilizer or methylene urea fertilizers), the more broadly distributed silica in vermiculite does not act to inhibit the formation of urea crystals.

In the fertilizer compositions described herein, the rice hulls may be present in a level such that the crystal aspect ratios of the crystals formed in the fertilizer are significantly reduced to effectively eliminate caking in the fertilizer. When the crystal aspect ratio growth rate is impaired, crystal size and relative strength is substantially reduced. In addition, the ability of the crystals to bond together is minimized, due to the overall shorter length of each crystal. The crystal aspect ratios of the crystals formed in the urea containing fertilizer (e.g., urea fertilizers or urea formaldehyde reaction product fertilizers such as urea-formaldehyde fertilizer or methylene urea fertilizers) described herein may be reduced to a level of about 5:1 as compared to urea containing fertilizer not containing ground rice hulls. The crystal aspect ratios of the crystals formed in the urea containing fertilizer (e.g., urea fertilizers or urea formaldehyde reaction product fertilizers such as urea-formaldehyde fertilizer or methylene urea fertilizers) may be reduced to a level of from about 30:1 to about 4:1, for example, 30:1, 27:1, 25:1, 23:1, 20:1, 19:1, 17:1, 16:1, 15:1, 13:1, 10:1, 9:1, 8:1, 7:1, 6:1, 5:1, or 4:1. These levels may be observed after storage, for example after a period of from 1 to 8 months of storage, e.g., 1, 2, 3, 4, 5, 6, 7, or 8 months after storage. Further, the urea crystal area formed after storage is reduced as compared to fertilizers not comprising rice hulls. For example, the average crystal area of urea crystals formed in said fertilizer after 2 months may be less than 30, 40, or 50 $\mu m^2$.

Urea crystal formation in urea-based fertilizer may be measured using Automated Segmentation Analysis using, for example, a scanning electron microscope (SEM). Scanning electron images of the surface of urea containing fertilizer (e.g., urea fertilizers or urea formaldehyde reaction product fertilizers such as urea-formaldehyde fertilizer or methylene urea fertilizers) typically show urea crystal growth after aging for several months. Automated Segmentation Analysis provides for the quantitative measurement and counting of the number of crystals on the surface, without altering the crystals.

The SEM used for acquiring the images of urea crystals may be set with variable pressure or low pressure operational modes. The standard SEM sample chamber conditions can have pressures of $1\times10^{-6}$ Torr at room temperature (e.g., about 25° C.). Under these conditions the ratio of the vapor pressure of urea and chamber pressure becomes high enough that urea crystals are unstable and sublimation begins, creating sample artifacts that eliminate or significantly reduce the measureable quantity of urea crystals. This phenomenon can essentially, destroy the original aged sample integrity, leading to false interpretation of aging effects. In order the maintain urea crystal stability, a sample chamber pressure should be no greater than 50-80 pascal, with a sample temperatures ranging from about −25 to −27° C. The sample temperature may be maintained using a Peltier cooling stage that operates within the SEM sample chamber.

The first step in the process of measuring crystal formation is to acquire the scanning electron image. The image may be acquired using a quad-coordinate Backscatter detector. This detector provides a grey-scale image of the sample and assigns grey-scale values to specific areas on the image based on the atomic number distribution on the sample. The Backscatter detector also provides topographical imaging of the surface of the sample.

The atomic number based grey-scale assignment helps distinguish the composition of the crystals, which is primarily urea, from the composition of the fertilizer surface. When investigating fertilizers with particle sizes ranging from 0.5-3.0 mm in mean diameter, it is preferred to utilize at least 400× magnification and for further crystal definition it is more preferred to use a magnification of 1200×.

Once the images have been acquired, they can be imported into an image analysis software, such Image Pro Plus (Media Cybernetics, Silver Spring, Md.) The next step is to complete an image segmentation analysis where the grey scale pixels assigned to the urea crystals are separated from other grey scale values within the fertilizer surface. The software allows for 256 shades of grey for analysis. Assigning a grey scale range to the urea crystals may be done by manually looking at the sample image and comparing that image to a histogram showing the distribution of the shades of grey found in the image. For example, if the urea crystals appeared to be consistent with a grey scale range 113-120 then that range of pixels would be assigned to the area of interest. Once the range is defined for the urea crystals the next step is to remove the background pixels. The grey scale pixels of the fertilizer surface are defined as background, therefore, grey scale ranges 0-112 and 121-256 are assigned a completely different color, such as red. This leaves a segmented image with just urea crystals and red background.

The next step is to use the Image Pro Plus software to measure and count the crystals in the image area. The program employs several mathematical algorithms to generate key data values such as, aspect ratio, area, number and statistical values like mean and standard deviation. This data is utilized to establish numerical differences between image samples without destroying the integrity of the original sample.

The rice hulls may comminuted in size by grinding. The rice hulls may be comminuted to a size on average of about 20-70 SGN, 30-60 SGN, 45-55 SGN, 30-50 SGN, 40-60 SGN, 45-50 SGN, or 50-55 SGN in size. The rice hulls may be comminuted to a size of about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70 SGN in size. In specific embodiment, the rice hulls may be comminuted to a size of about 48-53 SGN in size. In another specific embodiment, the rice hulls may be comminuted to a size of about 50 SGN in size.

The rice hulls may be present in an amount sufficient to decrease urea crystal formation in urea-based fertilizer. For example, the rice hulls may be about 5-50% by weight of the granule. The rice hulls may be about 10-40%, 20-30%, 15-30%, 20-35%, 15-40%, 15-30%, 10-20%, 10-25%, 15-25%, 15-35%, 25-50%, or 15-50% by weight of the granule. In the fertilizer compositions described herein, the rice hulls may be about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% by weight of the granule. In specific embodiment, the fertilizer composition may comprise about 10-25% rice hulls by weight of the granule. In another specific embodiment, the fertilizer composition may comprise about 20% rice hulls by weight of the granule. The fertilizer composition may be granular, comprising a granule of urea-fertilizer and ground rice hulls.

The fertilizer granules may comprise rice hulls and a urea containing fertilizer (e.g., urea fertilizers or urea formaldehyde reaction product fertilizers such as urea-formaldehyde fertilizer or methylene urea fertilizers). For example, the granule may comprise ground rice hulls and urea containing fertilizer (e.g., urea fertilizers or urea formaldehyde reaction product fertilizers such as urea-formaldehyde fertilizer or methylene urea fertilizers). The ground rice hulls may be sprayed or soaked in methylene urea to coat them with the urea-fertilizer.

The fertilizer composition may comprise granules comprising rice hulls and a urea containing fertilizer (e.g., urea fertilizers or urea formaldehyde reaction product fertilizers such as urea-formaldehyde fertilizer or methylene urea fertilizers). The granules may further comprise other components, including but not limited to macronutrients, micronutrients, carriers (e.g., inert solid carriers), biostimulants, and other fertilizers. These components may be part of the granule or they may be admixed with the granules comprising rice hulls and a urea containing fertilizer (e.g., urea fertilizers or urea formaldehyde reaction product fertilizers such as urea-formaldehyde fertilizer or methylene urea fertilizers).

Fertilizer Components

The fertilizer compositions described herein may comprise three macronutrients: nitrogen (N), phosphorus (P), potassium (K); three secondary macronutrients: calcium (Ca), magnesium (Mg), and sulfur (S); and micronutrients including, but not limited to, copper (Cu), iron (Fe), manganese (Mn), molybdenum (Mo), zinc (Zn); nickel (Ni), boron (B), silicon, cobalt (Co), and mixtures thereof.

The fertilizer components may be present in an amount sufficient to provide nutrients to a plant to support growth. The fertilizer components may range from about 1 to about 40% by weight elemental nitrogen (N) (preferably, about 15-36% by weight); about 1 to about 30% by weight phosphorous, e.g., as $P_2O_5$ (preferably, about 1-27% by weight); and about 1 to about 30% by weight potassium, e.g., as $K_2O$ (preferably, about 3-15% by weight). The micronutrient content of the fertilizer ingredient may range from about 1 to about 60,000 ppm (parts per million). For example, the micronutrient content may be about 10 to 20,000 ppm (parts per million).

The fertilizer compositions described herein may be a single nutrient fertilizer, comprising, for example, urea. The fertilizer compositions described herein may be a binary nutrient fertilizer providing both a nitrogen and phosphorous source. The fertilizer compositions described herein may be a NPK nutrient fertilizer providing both a nitrogen, potassium, and phosphorous source.

The fertilizer compositions described herein may comprise micronutrients. For example, the fertilizer compositions may comprise potassium sulfate, micro elements, mono-ammonium phosphate, potassium chloride, or mixtures thereof. The fertilizer compositions may comprise calcium nitrate, ammonium sulfate, isobutylidene dirurea, ammonium nitrate, ureaform, methylene urea, urea, anhydrous ammonia, polymer coated urea (e.g. sulfur coated urea) ammonium polyphophate, monoammonium phosphate, iron, diammonium phosphate, potassium nitrate, or mixtures thereof.

In one embodiment, the fertilizer composition may comprise granules comprising ground rice hulls coated with a urea containing fertilizer resin (e.g., a resin of urea fertilizers or urea formaldehyde reaction product fertilizers such as urea-formaldehyde fertilizer or methylene urea fertilizers), potassium sulfate, ammonium sulfate, 3,6-Dichloro-2-methoxybenzoic acid (dicamba), 2,4-dichlorophenoxy acetic acid (2,4-D), and/or methyl chlorophenoxy propionic acid (MCPP-P). For example, the granule may comprise 40-60% by weight urea containing fertilizer (e.g., urea fertilizers or urea formaldehyde reaction product fertilizers such as urea-formaldehyde fertilizer or methylene urea fertilizers) and 10-25% by weight ground rice hulls, e.g., about 58% by weight urea containing fertilizer and 20% by weight ground rice hulls. The granule may comprise about 5-10% by weight potassium sulfate, e.g., about 6.5% by weight potassium sulfate. The granule may comprise about 10-20% by weight ammonium sulfate, e.g., about 13.5% by weight ammonium sulfate. The granule may comprise about 0.5-4% by weight 2,4-dichlorophenoxy acetic acid (2,4-D), e.g., about 1.25% 2,4-D, 0.04-0.2% by weight 3,6-Dichloro-2-methoxybenzoic acid (dicamba), and/or 0.5-1.5% by weight methyl chlorophenoxy propionic acid (MCPP-P), e.g., about 0.7% MCPP-P.

In one embodiment, the fertilizer composition may further comprise potassium sulfate, ammonium sulfate, 3,6-Dichloro-2-methoxybenzoic acid (dicamba), 2,4-dichlorophenoxy acetic acid (2,4-D), and/or methyl chlorophenoxy propionic acid (MCPP-P). For example, the fertilizer composition may comprise about 5-10% by weight potassium sulfate, e.g., about 6.5% by weight potassium sulfate. The fertilizer composition may comprise about 10-20% by weight ammonium sulfate, e.g., about 13.5% by weight ammonium sulfate. The fertilizer composition may comprise about 0.5-4% by weight 2,4-dichlorophenoxy acetic acid (2,4-D), e.g., about 1.25% 2,4-D, 0.04-0.2% by weight 3,6-Dichloro-2-methoxybenzoic acid (dicamba), and/or 0.5-1.5% by weight methyl chlorophenoxy propionic acid (MCPP-P), e.g., about 0.7% MCPP-P.

The fertilizer compositions described herein may comprise methylene urea (MU) resin. The MU resin may have an urea to formaldehyde ratio of about 1.5:1 to 8:1. The urea to formaldehyde ratio may be from about 1.5:1 to about 8:1, for example, 1.5:1, 2:1, 3:1, 4:1, 5:1, 6:1, 7:1, or 8:1. The urea to formaldehyde ratio may be about 4:1.

The fertilizer compositions described herein may comprise less than 1, less than 2, less than 3, less than 4, less than 5, less than 6, less than 7, less than 8, less than 9, less than 10, less than 11, less than 12, less than 13, less than 14, less than 15, less than 16, less than 17, less than 18, or less than 20% water by weight of the composition. In a specific embodiment, the fertilizer compositions described herein may comprise less than 5% water by weight of the composition.

The fertilizer compositions described herein encompass a wide variety of fertilizer forms including, but not limited to granules, particles, or pellets (referred to collectively as fertilizer granule). The physical forms of the fertilizer compositions described herein include granules and extruded particles. The fertilizer compositions described herein may be a granular composition. Fertilizer granule sizes may range from about 0.5 to about 5.0 mm diameter (e.g., about 0.5-2 mm). Fertilizer granule sizes may range from about 1.0 to about 5.0 mm diameter (e.g., about 1-3.0 mm). Fertilizer granule sizes may range from about 0.5 to about 2 mm (e.g., about 1.0-5.0 mm).

The granular particles may be about 0.5-5 mm in size, for example, 0.5, 0.6, 0.7, 0.8, 0.9, 1, 1.25, 1.5, 1.75, 2, 2.25, 2.5, 2.75, 3, 4, 5 mm in size. The granular particles may be about 1-5, 1-2, 0.5-5, 0.5-2, 1-3, 2-5, 1-4, 2-4, or 3-5 mm in size. In another specific embodiment, the granular particles may be about 0.5-4 mm in size as measured by diameter.

The fertilizer compositions described herein may be a controlled release fertilizer.

The fertilizer compositions described herein may be admixed with herbicides, micronutrients, biostimulants, soil amendments, and inert solid carriers.

Inert solid carriers may be admixed with the fertilizer components to produce a composition described herein. Suitable inert solid carrier materials include a variety of organic and/or inorganic materials, which absorb or which may be coated with the active ingredient and that have been appropriately ground/fractionated/sized, may be employed herein. Suitable organic materials include but are not limited to corncobs, peanut hulls, processed paper pulp, sawdust, and mixtures thereof. Suitable inorganic materials include limestone, gypsum, sand, vermiculite, perlite, fuller's earth and clays such as attapulgite clays, bentonite clays, montmorillonite clays, and mixtures thereof.

The fertilizer compositions may be admixed with herbicides including, but not limited to, 2,4-dichlorophenoxy acetic acid (2,4-D), methyl chlorophenoxy propionic acid (MCPP-P), 3,6-Dichloro-2-methoxybenzoic acid (dicamba), amide herbicides including, but not limited to, allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, napropamide-N, naptalam, pethoxamid, propyzamide, quinonamid, saflufenacil, tebutam and tiafenacil; anilide herbicides including, but not limited to, chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides including, but not limited to, benzoylprop, flamprop and flamprop-M; chloroacetanilide herbicides including, but not limited to, acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides including, but not limited to, benzofluor, perfluidone, pyrimisulfan and profluazol; sulfonamide herbicides including, but not limited to, asulam, carbasulam, fenasulam and oryzalin; antibiotic herbicides including, but not limited to, bilanafos; benzoic acid herbicides such as chloramben, dicamba, 2,3,6-TBA and tricamba; pyrimidinyloxybenzoic acid herbicides including, but not limited to, bispyribac and pyriminobac; pyrimidinylthiobenzoic acid herbicides including, but not limited to, pyrithiobac; phthalic acid herbicides including, but not limited to, chlorthal; picolinic acid herbicides including, but not limited to, aminopyralid, clopyralid, halauxifen and picloram; quinolinecarboxylic acid herbicides including, but not limited to, quinclorac and quinmerac; benzoylcyclohexanedione herbicides including, but not limited to, mesotrione, sulcotrione and tembotrione; benzofuranyl alkylsulfonate herbicides including, but not limited to, benfuresate and ethofumesate; carbamate herbicides including, but not limited to, asulam, carboxazole, chlorprocarb, dichlormate, fenasulam, karbutilate and terbucarb; carbanilate herbicides including, but not limited to, barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides including, but not limited to, alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides including, but not limited to, benzfendizone, cinidon-ethyl, flumezin, flumiclorac, flumioxazin and flumipropyn; dinitroaniline herbicides including, but not limited to, benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides including, but not limited to, dinofenate, dinoprop, dinosam, dinoseb, dinoterb, DNOC, etinofen and medinoterb; diphenyl ether herbicides including, but not limited to, ethoxyfen; nitrophenyl ether herbicides including, but not limited to, acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides including, but not limited to, dazomet and metam; halogenated aliphatic herbicides including, but not limited to, alorac, chloropon, dalapon, flupropanate, hexachloroacetone, iodomethane, methyl bromide, monochloroacetic acid, sodium chloroacetate an trichloroacetic acid; imidazolinone herbicides including, but not limited to, imazamethabenz, imazamox, imazapic, imazapyr, imazaquin and imazethapyr; inorganic herbicides including, but not limited to, ammonium sulfamate, borax, calcium chlorate, copper sulfate, ferrous sulfate, potassium azide, potassium cyanate, sodium azide, sodium chlorate and sulfuric acid; nitrite herbicides such as bromobonil, bromoxynil, chloroxynil, dichlobenil, iodobonil, ioxynil and pyraclonil; organophosphorous herbicides including, but not limited to, amiprofos-methyl, anilofos, bensulide, bilanafos, butamifos, 2,4-DEP, DMPA, EBEP, fosamine, glufosinate, glufosinate-P, glyphosate and piperophos; oxadiazolone herbicides including, but not limited to, dimefuron, methazole, oxadiargyl and oxadiazon; oxazole herbicides including, but not limited to, carboxazole, fenoxasulfone, methiozolin and pyroxasulfone; phenoxy herbicides including, but not limited to, bromofenoxim, clomeprop, 2,4-DEB, 2,4-DEP, difenopenten, disul, erbon, etnipromid, fenteracol and trifopsime; phenoxyacetic herbicides including, but not limited to, 2,4-D, MCPA, MCPA-thioethyl and 2,4,5-T; phenoxybutyric herbicides; phenoxypropionic herbicides including, but not limited to, cloprop, 4-CPP, dichlorprop, dichlorprop-P, 3,4-DP, fenoprop, mecoprop and mecoprop-P; aryloxyphenoxypropionic herbicides including, but not limited to, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides including, but not limited to, dinitramine and prodiamine; phenyl pyrazolyl ketone herbicides including, but not limited to, benzofenap, pyrazolynate, pyrasulfotole, pyrazoxyfen and topramezone; pyrazolylphenyl herbicides including, but not limited to, fluazolate, pinoxaden and pyraflufen; pyridazine herbicides including, but not limited to, credazine, pyridafol and pyridate; pyridazinone herbicides such as brompyrazon, chloridazon, dimidazon, flufenpyr, metflurazon, norflurazon, oxapyrazon and pydanon; pyridine herbicides including, but not limited to, aminopyralid, cliodinate, clopyralid, dithiopyr, fluroxypyr, haloxydine, picloram, picolinafen, pyriclor, thiazopyr and triclopyr; pyrimidinediamine herbicides including, but not limited to, iprymidam and tioclorim; quaternary ammonium herbicides including, but not limited to, cyperquat, diethamquat, difenzoquat, diquat, morfamquat and paraquat; thiocarbamate herbicides including, but not limited to, butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides including, but not limited to, dimexano, EXD and proxan; thiourea herbicides including, but not limited to, methiuron; triazine herbicides such as dipropetryn, triaziflam and trihydroxytriazine; chlorotriazine herbicides including, but not limited to, atrazine, chlorazine, cyanazine, cyprazine, eglinazine, ipazine, mesoprazine, procyazine, proglinazine, propazine, sebuthylazine, simazine, terbuthylazine and trietazine; fluoroalkyltriazine herbicides including, but not limited to, indaziflam and traiziflam; methoxytriazine herbicides including, but not limited to, atraton, methometon, prometon, secbumeton, simeton and terbumeton; methylthiotriazine herbicides including, but not limited to, ametryn, aziprotryne, cyanatryn, desmetryn, dimethametryn, methoprotryne, prometryn, simetryn and terbutryn; triazinone herbicides including, but not limited to, ametridione, amibuzin, hexazinone, isomethiozin, metamitron and metribuzin; triazole herbicides such as amitrole, cafenstrole, epronaz and flupoxam; triazolone herbicides including, but not limited to, amicarbazone, bencarbazone, carfentrazone, flucarbazone, propoxycarbazone, sulfentrazone and thiencarbazone-methyl; triazolopyrimidine herbicides including, but not limited to, cloransulam, diclosulam, florasulam, flumetsulam, metosulam, penoxsulam; pyroxsulam; uracil herbicides including, but not limited to, butafenacil, bromacil, flupropacil, isocil, lenacil and terbacil; 3-phenyluracils; urea herbicides including, but not limited to, benzthiazuron, cumyluron, cycluron, dichloralurea, diflufenzopyr, isonoruron, isouron, methabenzthiazuron, monisouron and noruron; phenylurea herbicides including, but not limited to, anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides including, but not limited to, amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, propyrisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides including, but not limited to, buthiuron, ethidimuron, tebuthiuron, thiazafluron and thidiazuron; herbicides including, but not limited to, acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, citmethylin, clomazone, CPMF, cresol, ortho-dichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac; or mixtures thereof.

The fertilizer compositions can be applied at various rates to achieve the desired effect of weed control and turf safety. In general, a minimum of about 0.1-3 lb, e.g, about 1.5 lb active ingredient (e.g., 2,4-dichlorophenoxy acetic acid (2,4-D)) per acre is required to control weeds in turfgrass under the wide range of conditions that are experienced in growing turf, such as geographical location, temperature, soil moisture, weed species and stage of growth, and other factors.

The invention also provides for soil, soil amendments, and soil additives comprising the compositions described herein.

The fertilizer compositions described herein have a lower average odor concentration, as measured by odor unit per cubic meter of air (1 o.u./m$^3$), than other fertilizer compositions that do not comprise rice hulls. For example, the fertilizer compositions described herein may have less than 600 o.u./m$^3$, less than 590 o.u./m$^3$, less than 580 o.u./m$^3$, less than 570 o.u./m³, less than 560 o.u./m³, less than 550 o.u./m³, or less than 540 o.u./m³. In other embodiments, the fertilizer compositions have an average odor concentration of 530-550 o.u./m³ or 530-540 o.u./m³.

Methods of Making

The fertilizer compositions described herein may be manufactured by spraying urea containing fertilizer resin (e.g., a resin of urea fertilizers or urea formaldehyde reaction product fertilizers such as urea-formaldehyde fertilizer or methylene urea fertilizers) onto rice hulls and forming a granule. The rice may be hulled by dry milling or parboiling to yield rice hulls. The rice hulls may be ground to reduce them in size to any of the sizes discussed herein, such as about 20-70 SGN, about 30-60 SGN in size, or about 50 SGN in size, for example about 40, 41, 42, 43, 44, 45, 46, 47, 48, 49, 50, 51, 52, 53, 54, 55, 56, 57, 58, 59, or 60 SGN. Rice hulls may be granulated using a rotating drum, fluidized bed, pan, pug mill, or pellet mill. Fertilizer nutrients, including but not limited to, potassium sulfate, micro elements, mono-ammonium phosphate, potassium chloride, or mixtures thereof may be added to the fertilizer composition.

The fertilizer compositions described herein may be produced by employing any of a variety of processes. For example, a urea containing fertilizer resin (e.g., a resin of urea fertilizers or urea formaldehyde reaction product fertilizers such as urea-formaldehyde fertilizer or methylene urea fertilizers) can be applied to a ground rice hulls using: (a) a spray mixture with solvents and/or surfactants; (b) adhered to the outer surface of the rice hull granules with an adhesive/sticking agent; (c) incorporated into a mixture of dry ingredients and a liquid, and then extruded or molded into discrete particles; or (d) impregnated into a porous granule.

Specifically, the fertilizer compositions described herein may be prepared by mixing urea containing fertilizer resin (e.g., a resin of urea fertilizers or urea formaldehyde reaction product fertilizers such as urea-formaldehyde fertilizer or methylene urea fertilizers) in effective amounts with rice hulls (for example, in a rotating drum container) for a sufficient period of time, e.g., 1-10 minutes, until the urea containing fertilizer resin (e.g., a resin of urea fertilizers or urea formaldehyde reaction product fertilizers such as urea-formaldehyde fertilizer or methylene urea fertilizers) is uniformly coated on and absorbed into the rice hull granules. In one embodiment, the fertilizer composition manufactured may be granular with a particle size of about 0.5-10 mm, e.g., 0.8-4 mm. In an embodiment, the granulation may be done in a rotating drum at a temperature from about 100-200° F., for example 130-160° F. In an embodiment, the granulation may be performed in a series of rotating drums at a temperature of about 130-160° F.

Other optional methods which may be employed for producing compositions containing urea containing fertilizer (e.g., urea fertilizers or urea formaldehyde reaction product fertilizers such as urea-formaldehyde fertilizer or methylene urea fertilizers) and granular rice hulls include: dissolving a urea containing fertilizer resin (e.g., a resin of urea fertilizers or urea formaldehyde reaction product fertilizers such as urea-formaldehyde fertilizer or methylene urea fertilizers) concentrate in a liquid solvent/surfactant blend, e.g., water to make aqueous resin solution, then spraying this mixture onto ground rice hulls so the solution is uniformly absorbed on the substrate particles; or using urea containing fertilizer (e.g., urea fertilizers or urea formaldehyde reaction product fertilizers such as urea-formaldehyde fertilizer or methylene urea fertilizers) in a dry powder state, tacking this onto the surface of a fertilizer and/or inert carrier material, such as ground rice hulls, using a liquid sticking agent or adhesive to obtain a uniform distribution of the urea containing fertilizer (e.g., urea fertilizers or urea formaldehyde reaction product fertilizers such as urea-formaldehyde fertilizer or methylene urea fertilizers) over the substrate particles (e.g., ground rice hulls). For example, a molten urea containing fertilizer resin (e.g., a resin of urea fertilizers or urea formaldehyde reaction product fertilizers such as urea-formaldehyde fertilizer or methylene urea fertilizers) at a temperature of about 270-275° F. may be sprayed onto the rice hulls. See U.S. Pat. Nos. 5,102,440; 6,254,655; and 8,288,320, each of which are herein incorporated by reference in their entireties.

A method of making a soil comprising any of the compositions described herein is provided. In one embodiment, the method comprises admixing a soil with any of compositions described herein to form a soil comprising the compositions described herein.

Methods of Use

The fertilizer compositions described herein may be used to deliver nutrients to a plant. For example, a method of fertilizing a plant may comprise adding the fertilizer composition described herein to a plant. A method of feeding a plant may comprise adding the fertilizer composition described herein to a plant. A method of promoting plant growing may comprise adding the fertilizer composition described herein to a plant. The fertilizer compositions described herein an unexpected advantage over the prior art technology because the reduction in caking during product storage allows for achieves greater active ingredient delivery and thus, performance.

The fertilizer compositions described herein may be used in methods of feeding, promoting plant growth, or fertilizing a plant life comprising adding the fertilizer composition described herein to a plant life or an area containing the plant life. An area containing a plant life may include a lawn or garden.

A method of growing a plant life is also provided. In one embodiment, the method comprises growing a plant life in soil comprising any of the compositions described herein. In another embodiment, the method comprises preparing a soil comprising any of the compositions described herein and planting a plant life in said soil.

A method for reducing crystal formation after storage in a urea-based fertilizer comprising forming granules comprising rice hulls, and urea containing fertilizer (e.g., urea fertilizers or urea formaldehyde reaction product fertilizers such as urea-formaldehyde fertilizer or methylene urea fertilizers) resin. In another embodiment, a method for reducing the average crystal area formed after storage in a urea-based fertilizer comprising forming granules comprising rice hulls, and urea containing fertilizer (e.g., urea fertilizers or urea formaldehyde reaction product fertilizers such as urea-formaldehyde fertilizer or methylene urea fertilizers). In one embodiment, the rice hulls may be ground rice hulls, preferably about 40-60 SGN in size. In another embodiment, the storage may be for 1-8 months, e.g., 1, 2, 3, 4, 5, 6, 7, or 8 months.

A method for reducing the number of urea crystals formed in a fertilizer may comprise adding rice hulls in an amount sufficient to lower the crystal aspect ratios of the crystals formed in the fertilizer after storage. The number of urea crystals formed in the urea containing fertilizer (e.g., urea fertilizers or urea formaldehyde reaction product fertilizers such as urea-formaldehyde fertilizer or methylene urea fertilizers) may be reduced by about 10-40% as compared to a fertilizer not comprising rice hulls. The number of urea crystals formed in the urea containing fertilizer (e.g., urea fertilizers or urea formaldehyde reaction product fertilizers such as urea-formaldehyde fertilizer or methylene urea fertilizers) may be reduced by about 10%, 15%, 20%, 25%, 30%, 35%, or 40% as compared to a fertilizer not comprising rice hulls. The number of urea crystals formed in the urea containing fertilizer (e.g., urea fertilizers or urea formaldehyde reaction product fertilizers such as urea-formaldehyde fertilizer or methylene urea fertilizers) may be reduced after about 1-8 months of storage as compared a fertilizer not comprising rice hulls. The number of urea crystals formed in the urea containing fertilizer (e.g., urea fertilizers or urea formaldehyde reaction product fertilizers such as urea-formaldehyde fertilizer or methylene urea fertilizers) may be reduced after about 1, 2, 3, 4, 5, 6, 7, or 8 months of storage as compared a fertilizer not comprising rice hulls.

A method for increased weed control as compared to a fertilizer composition not comprising rice hulls comprising adding a fertilizer composition described herein to a plant life. The weed control may be improved by about 10, 15, 20, 25, 30, 35, 40, 45, or 50% as compared to a fertilizer composition not comprising rice hulls.

The plant life may be a plant, plant cutting, or seed. The plant may be young plant, transplant, or seedling.

All publications (e.g., Non-Patent Literature), patents, patent application publications, and patent applications are herein incorporated by reference to the same extent as if each individual publication, patent, patent application publication, or patent application was specifically and individually indicated to be incorporated by reference.

Although methods and materials similar or equivalent to those described herein may be used in the invention or testing of the present invention, suitable methods and materials are described herein. The materials, methods and examples are illustrative only, and are not intended to be limiting.

The following examples are included merely for purposes of illustration of certain aspects and embodiments of the present invention, and are not intended to limit the invention.

EXAMPLES

Example 1

Rice Hull Urea Containing Fertilizer Composition

Rice hulls were ground and classified to a −20 Mesh/+80 mesh size fraction, yielding an average particle size of 30-40 SGN. The ground hulls were then formulated with methylene urea resin using a granulation process. The amount of ground rice hulls was about 15-25% by weight of the entire formulation. The granulation process was conducted by adding dry ground rice hulls, along with other dry fertilizer nutrients such potassium sulfate, micro elements, mono-ammonium phosphate, or potassium chloride and spraying the solids with a molten methylene urea resin. The resin served as a binder to help form granules, in addition to a fertilizer ingredient. The methylene urea resin temperature was in a range of 270-275° F., and containing less than 5% moisture. The methylene urea resin was formulated with a urea to formaldehyde ratio of 4:1 to 8:1. The granulation process was conducted in a rotating drum at a temperature from 130-160° F.

Once the granulation process was completed, the materials were screened to a size most appropriate for a given product category. The size and density of the rice hulls makes it possible to manufacture highly effective granular weed control products, using granulation technology. Size −14 mesh +50 mesh was used and provided a good combination of agronomic performance and processability.

Once the granulation process and screening was completed, an active ingredient solution or melt was applied to the surface using a continuous or batch mixer/blender.

The fertilizer composition comprising granulated methylene urea fertilizer/ground rice hulls ("Experimental") and granulated methylene urea fertilizer (used as a control, "Current") were aged for 5 months. The fertilizers were then examined for the appearance of crystals and the size of the crystals before and after aging. The crystals were measured using Automated Segmentation Analysis as described herein.

TABLE 1

| Crystal Formation | | | |
|---|---|---|---|
| Sample Description | Additive Type | Crystal Area ($\mu m^2$) | Crystals Counted (#) |
| Fresh TB + 2, Current | None | 7.46 | 477 |
| Aged TB + 2, Current | None | 97.33 | 1,976 |
| Fresh TB + 2, Experimental | Rice Hulls | 16.36 | 612 |
| Aged TB + 2, Experimental | Rice Hulls | 30.49 | 1,149 |

As shown above, the addition of ground rice hulls significantly reduced the crystal area and crystals counted compared to a fertilizer composition lacking rice hulls after five months of storage. As such, the ground rice hulls significantly reduced urea crystal growth. This lower crystal growth helped prevent the development of crystal bridges, which form from the base elements of product caking.

Example 2

Urea Crystal Inhibition

Formulation samples prepared with 20% rice hulls, potassium sulfate, herbicide, and coated with urea-formaldehyde resin were placed into individual bags weighing 14.29 pounds each. These bags were palletized and stacked with 80 bags on each pallet. The pallets were then stacked four high and placed in a warehouse in order to evaluate storage stability. A similar formulation, prepared with 20% vermiculite, potassium sulfate, mono-ammonium phosphate, herbicide, and coated with urea-formaldehyde resin was placed into individual bags weighing 14.29 pounds each. This formulation was palletized and stored in the same manner as the rice hull based formula.

Figure 2A:
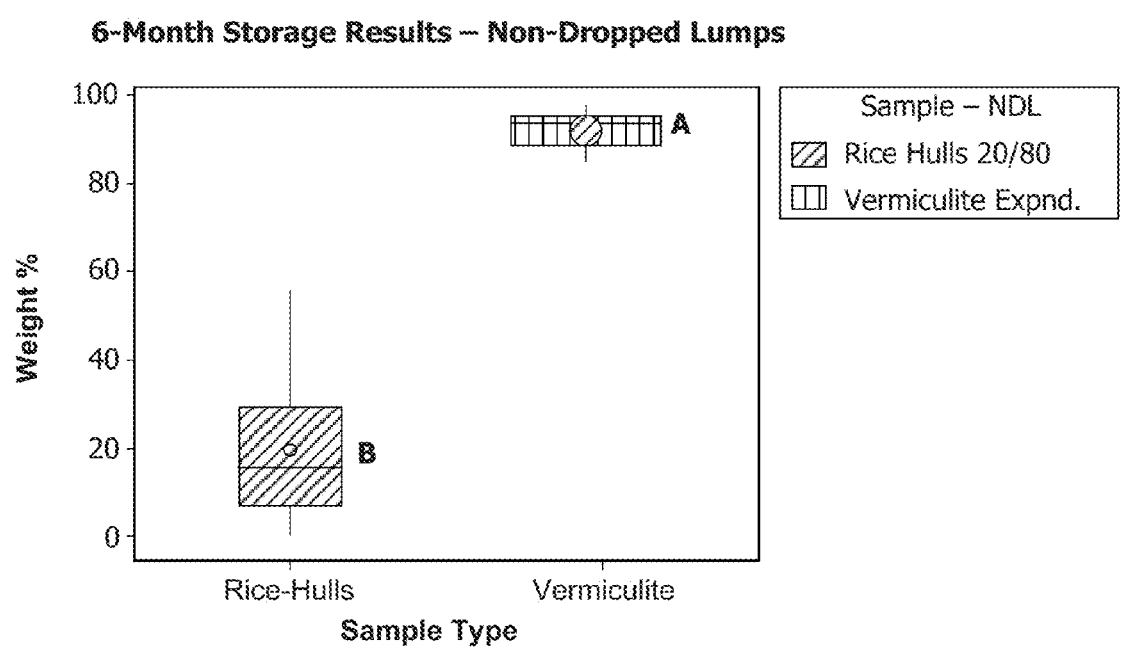
FIG. 2A depicts the results from non-dropped lumps test and a dropped lumps test for fertilizer stored 6 months using one formulation comprising 20% ground rice hulls, potassium sulfate, herbicide, and coated with urea-formaldehyde (UF) resin, and a second formulation comprising 20% vermiculite, potassium sulfate, mono-ammonium phosphate, herbicide, and coated with UF resin.
Figure 2B:
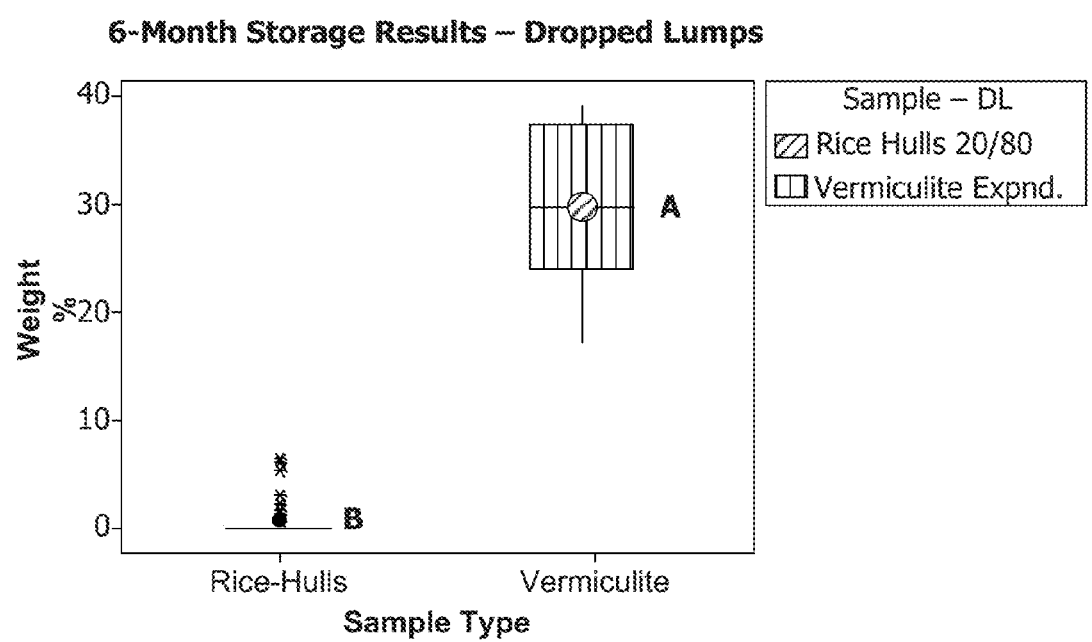
FIG. 2B depicts the results from non-dropped lumps test and a dropped lumps test for fertilizer stored 6 months using one formulation comprising 20% ground rice hulls, potassium sulfate, herbicide, and coated with urea-formaldehyde (UF) resin, and a second formulation comprising 20% vermiculite, potassium sulfate, mono-ammonium phosphate, herbicide, and coated with UF resin.

Following six months of storage in the warehouse, bags were removed from the 2-down pallet and the 4-down pallet for evaluation. The primary method of evaluation was to establish the weight of fertilizer lumps that would not pass through a 4-mesh screen. The lumps correspond to crystal formation. More crystal formation increases the agglomeration of urea crystals to form lumps, e.g., very large collections of urea crystals. The weight evaluation was conducted on bags that were not handled prior to weighing the lumps: non-dropped Lumps (FIG. 2A). In addition, the weight evaluation was conducted after dropping the each bag from a waist high position one time. This dropped test simulates a typical consumer handling scenario. The weight evaluation on the handled bags was referred to, Dropped Lumps. Each test included 40 data points (FIG. 2B).

MiniTab statistical software was used to analyze the raw data. Box plots were utilized to show the data sample distribution and the boxes contain 75% of the data values.

The final data tails are shown by whisker lines and/or single points. The mean value is shown by the solid circle within the box. The means were compared using one-way ANOVA and Tukey methods. Means that do not share a letter are considered significantly different.

The fertilizer composition comprising rice hulls had significantly fewer non-dropped lumps and dropped lumps after 6 months of storage as compared to a fertilizer composition comprising vermiculite. The fertilizer compositions comprising rice hulls and a urea-based fertilizer surprisingly provided lower crystal formation and smaller crystals over a 6 month-storage period as compared to a urea-based fertilizer alone.

Example 3

Field Test Data on Weed Control

Herbicide control efficacy trials were conducted comparing a methylene urea based fertilizer with an herbicide without ground rice hulls—Granular Weed & Feed "Granular W&F" was compared to a methylene urea based fertilizer with an herbicide with 20% ground rice hulls by weight—"Rice Hull W&F." The fertilizer application rate for both materials was 0.8 Lbs. nitrogen per 1,000 square feet. The herbicide included in both materials was 1.5 Lbs. of 2,4-dichlorophenoxy acetic acid (2,4-D) and 1.5 Lbs. of methyl chlorophenoxy propionic acid (MCPP-P) per acre. The materials were applied to a Kentucky bluegrass area infested with Dandelion (*Taraxacum officinale*) and White clover (*Trifolium repens*).

The treatments were weighed in grams prior to application to maintain accurate product delivery rate and applied using a standardized screen distribution box which covered each test plot area. All treatments were applied on dew moistened foliage. Table 1 shows the results of trials conducted to determine Dandelion control and Table 2 shows the results of trials conducted to determine White clover control. All trials were replicated and weed control evaluations were conducted one month after application.

TABLE 3

White Clover (*Trifolium repens*)

|  | White clover (*Trifolium repens*) Control (%) - One Month After Application | | | |
|---|---|---|---|---|
| Trial | A | B | C | D |
| Untreated Control | 0.0 b* | 0.0 c | 0.0 c | 0.0 b |
| Granular W&F | 20.0 b | 36.3 b | 60.0 b | 20.0 b |
| Rice Hulls W&F | 63.8 a | 88.8 a | 78.8 a | 67.5 a |

*Means followed by same letter do not significantly differ (P = 0.05, LSD)

The results from trials conducted to determine extent of White clover control indicated the "Rice Hulls W&F" controlled White clover a rate of 1.3-3.4 times greater than "Granular W&F."

The fertilizer compositions comprising granules comprising rice hulls and a urea-based fertilizer surprisingly provided better weed control as compared to a urea-based fertilizer alone.

As discussed herein, the lower urea crystal growth also protects any surface applied active ingredients, since crystal will no longer cover the particle surface. In a field application, these urea crystals must dissolve before the active ingredient will come into contact with the target surface. Since there is only a limited amount of leaf surface moisture available, in many cases the active ingredient will never come in contact with the target surface, leading to decreased active ingredient performance. Therefore, another advantage of the fertilizer composition comprising ground rice hulls is that improved active ingredient effectiveness and product performance.

Example 4

Odor Analysis Study Summary

The odors from three fertilizer products, (1) a urea-based fertilizer "fertilizer," (2) a fertilizer with an herbicide without ground rice hulls—Granular Weed & Feed "Granular W&F," (3) a methylene urea based fertilizer with an herbicide with 20% ground rice hulls by weight—"Rice Hull

TABLE 2

Dandelion (*Taraxacum officinale*) Control

|  | Dandelion (*Taraxacum officinale*) Control (%) - One Month After Application | | | | | | | |
|---|---|---|---|---|---|---|---|---|
| Trial | A | B | C | D | E | F | G | H |
| Untreated Control | 0.0 c* | 0.0 c | 0.0 c | 0.0 c | 0.0 c | 0.0 c | 0.0 c | 0.0 c |
| Granular W&F | 17.5 b | 22.5 b | 47.5 b | 25.0 b | 35.0 b | 43.8 b | 37.5 b | 41.3 b |
| Rice Hulls W&F | 52.5 a | 42.5 a | 75.0 a | 50.0 a | 77.5 a | 86.3 a | 78.8 a | 76.3 a |

*Means followed by same letter do not significantly differ (P = 0.05, LSD)

The surprising results showed that the "Rice Hull W&F" controlled Dandelions at a rate of 1.6-3.0 times greater than "Granular W&F."

W&F," were evaluated. Both Granular W&F and Rice Hull W&F contained about 1.21% 2,4-Dichlorophenoxy Acetic Acid (2,4-D) by weight and 0.61% Methyl Chlorophenoxy Propionic Acid (MCPP-P) by weight herbicides. Both Granular W&F and Rice Hull W&F were prepared to have about 28% nitrogen by weight and about 3% $K_2O$ by weight. The odor characterization was done by olfactometric analysis on odorous samples prepared from the three products. The analysis provided the overall odor concentration.

Experimental Methods & Results

In order to capture odorous gas from each of the three samples, equal weights of each were placed in a small pan. Each pan is then covered by a gas flux chamber were a controlled flow of nitrogen gas introduced into the chamber. Simultaneously, the air is withdrawn into a 60 liter Nalophan sample bag. Three air samples were collected for each product under evaluation. The gas samples are adjusted to normalized temperature and pressure for olfactometry (P=101.3 kPa and T=293 K). The notation $Nm^3$ indicates the use of normalized gas.

The odors from the gas samples are quantified by olfactometeric analysis, which determines the olfactory perception threshold of a gaseous sample. The olfactory perception threshold is defined as the number of dilutions at which 50% of a panel perceives the odor while 50% do not perceive the odor. By definition, the olfactory perception threshold is equivalent to 1 odor unit per cubic meter of air '1 o.u./$m^3$'. The number of dilutions of the odor sample required to obtain 1 o.u./$m^3$ indicates the odor concentration of the sample. Based on these parameters, the odor concentration of each sample was tested and Table 4 summarizes the results.

TABLE 4

Odor Concentrations Measured

| Product | Average Odor Concentrations [o.u./$Nm^3$] |
|---|---|
| Fertilizer Only | 651 |
| Granular W&F | 557 |
| Rice Hull W&F | 534 |

The Rice Hulls W&F had the lowest mean value of 534 o.u./$Nm^3$. The fertilizer only, had the highest mean value of 651 o.u./$Nm^3$. Thus, the addition of ground rice hulls to the granules surprisingly reduced the production of volatile organic compounds that may be detected by humans as an odor.

Those skilled in the art will recognize, or be able to ascertain using no more than routine experimentation, many equivalents to the specific embodiments of the invention described herein. Such equivalents are intended to be encompassed by the following claims.

I claim:

1. A fertilizer composition comprising granules comprising a mixture of rice hulls and a urea containing fertilizer, wherein rice hulls reside within interior regions of the granules.

2. The composition of claim 1, wherein said urea containing fertilizer is a urea formaldehyde reaction product fertilizer.

3. The composition of claim 2, wherein said urea containing fertilizer is a methylene urea fertilizer.

4. The composition of claim 2, wherein said urea containing fertilizer is a urea-formaldehyde fertilizer.

5. The composition of claim 2, wherein said urea formaldehyde reaction product fertilizer has a urea to formaldehyde ratio of about 1.5:1 to about 8:1.

6. The composition of claim 1, wherein said rice hulls are about 20-70 SGN.

7. The composition of claim 1, wherein the fertilizer composition, when stored over 1, 2, 3, 4, 5, 6, 7, or 8 months, has a reduced crystal aspect ratio compared to a urea containing fertilizer composition not having rice hulls stored under the same conditions.

8. The composition of claim 7, wherein the crystal aspect ratio of said fertilizer composition is reduced to a level in a range from about 30:1 to about 4:1.

9. The composition of claim 1, wherein said rice hulls are about 1-50% by weight of the granule. 1.5:1 to about 8:1.

10. The composition of claim 1, wherein the fertilizer composition has an average crystal area of urea crystals of less than 60 $\mu m^2$ formed after 2, 3, 4, 5, 6, 7, or 8 months.

11. The composition of claim 1, wherein said composition comprises less than 20% water by weight of the composition.

12. The composition of claim 1, wherein said granules are about 0.5-5 mm in size.

13. The composition of claim 1, further comprising potassium sulfate, ammonium sulfate, 3,6-Dichloro-2-methoxybenzoic acid (dicamba), 2,4-dichlorophenoxy acetic acid (2,4-D), methyl chlorophenoxy propionic acid (MCPP-P), or mixtures thereof.

14. The composition of claim 13, wherein said granule comprises 0.5-4% by weight 2,4-dichlorophenoxy acetic acid (2,4-D), 0.5-1.5% by weight methyl chlorophenoxy propionic acid (MCPP-P), 0.04-0.2% by weight 3,6-Dichloro-2-methoxybenzoic acid (dicamba), or mixtures thereof.

15. The composition of claim 1, where said granule comprises 10-25% by weight ground rice hulls.

16. The composition of claim 1, wherein the fertilizer composition further comprises additional fertilizer components selected from the group consisting of calcium nitrate, ammonium sulfate, sulfur-coated urea, isobutylidene diurea, ammonium nitrate, ureaform, urea formaldehyde reaction product, urea, anhydrous ammonia, ammonium polyphosphate, monoammonium phosphate, diammonium phosphate, potassium nitrate, potassium sulfate, polymer coated urea, micro elements, mono-ammonium phosphate, potassium chloride, and mixtures thereof, herbicides, micronutrients, biostimulants, macronutrients, inert solid carriers, or mixtures thereof.

17. The composition of claim 1, wherein said composition has an average odor concentration of less than 550 o.u./$m^3$.

18. The composition of claim 1, wherein the urea containing fertilizer is within the interior of the granule.

19. The composition of claim 18, wherein said granule comprises 40-60% by weight urea containing fertilizer.

20. The composition of claim 1, wherein the urea containing fertilizer is coated onto the interior of the granule.

21. A method of making the composition of claim 20, comprising spraying the urea containing fertilizer onto the rice hull.

22. A method of fertilizing a plant comprising applying the composition of claim 1 to said plant.

* * * * *

UNITED STATES PATENT AND TRADEMARK OFFICE
CERTIFICATE OF CORRECTION

PATENT NO. : 9,663,412 B2  
APPLICATION NO. : 15/073181  
DATED : May 30, 2017  
INVENTOR(S) : Harold Thompson Page 1 of 1

It is certified that error appears in the above-identified patent and that said Letters Patent is hereby corrected as shown below:

In the Claims

Claim 9, Column 24, Line 16, replace "about 1-50% by weight of the granule. 1.5:1 to about 8:1." with -- about 1-50% by weight of the granule. --

Signed and Sealed this
Twentieth Day of November, 2018

Andrei Iancu
*Director of the United States Patent and Trademark Office*